US 8,485,965 B2

(12) United States Patent
Ito et al.

(10) Patent No.: US 8,485,965 B2
(45) Date of Patent: Jul. 16, 2013

(54) ENDOSCOPE MAIN BODY AND ENDOSCOPE

(75) Inventors: Yoshiaki Ito, Fuchu (JP); Taro Iede, Hachioji (JP); Hirokazu Tanaka, Hachioji (JP); Hideya Kitagawa, Hachioji (JP); Manabu Miyamoto, Musashino (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 1225 days.

(21) Appl. No.: 12/339,497

(22) Filed: Dec. 19, 2008

(65) Prior Publication Data
US 2009/0171160 A1    Jul. 2, 2009

Related U.S. Application Data

(60) Provisional application No. 61/009,703, filed on Dec. 31, 2007.

(30) Foreign Application Priority Data

Dec. 27, 2007   (JP) ................. 2007-338343

(51) Int. Cl.
*A61B 1/04* (2006.01)
*A61B 1/00* (2006.01)
(52) U.S. Cl.
USPC ................ 600/112; 600/113; 600/114
(58) Field of Classification Search
USPC .......... 600/104, 114, 121, 123, 146, 153, 600/112
See application file for complete search history.

(56) References Cited

U.S. PATENT DOCUMENTS

| 5,301,061 | A | | 4/1994 | Nakada et al. | |
|---|---|---|---|---|---|
| 5,820,546 | A | * | 10/1998 | Ouchi | 600/123 |
| 5,924,977 | A | | 7/1999 | Yabe et al. | |
| 5,976,074 | A | * | 11/1999 | Moriyama | 600/144 |
| 6,352,503 | B1 | | 3/2002 | Matsui et al. | |

(Continued)

FOREIGN PATENT DOCUMENTS

| JP | 6-66605 U | 9/1994 |
|---|---|---|
| JP | 2000-33071 A | 2/2000 |

(Continued)

OTHER PUBLICATIONS

Extended European Search Report dated May 8, 2009 (8 pages), issued in counterpart European Application Serial No. 08172718.2.

(Continued)

*Primary Examiner* — Philip R Smith
*Assistant Examiner* — William Chou
(74) *Attorney, Agent, or Firm* — Holtz, Holtz, Goodman & Chick, P.C.

(57) ABSTRACT

An endoscope main body constituting an endoscope in a state in which an elongated detachable observation optical system is attached to the endoscope main body, and in a proximal end of an insertion section of the endoscope main body, a branch member is disposed. The branch member is provided so that a first extended section and a second extended section are branched from each other and thereby first and second operating sections are separately arranged. Furthermore, the branch member has an opening as an inlet which guides an imaging module in a distal end of the observation optical system to a hard portion of the insertion section.

9 Claims, 10 Drawing Sheets

U.S. PATENT DOCUMENTS

| | | | |
|---|---|---|---|
| 7,223,231 B2 * | 5/2007 | Akiba | 600/130 |
| 7,371,211 B2 * | 5/2008 | Akiba | 600/156 |
| 7,922,650 B2 * | 4/2011 | McWeeney et al. | 600/104 |
| 8,083,667 B2 * | 12/2011 | Cooper et al. | 600/104 |
| 2003/0176767 A1 | 9/2003 | Long et al. | |
| 2005/0027165 A1 * | 2/2005 | Rovegno | 600/154 |
| 2005/0065397 A1 * | 3/2005 | Saadat et al. | 600/104 |
| 2005/0090709 A1 | 4/2005 | Okada et al. | |
| 2007/0167680 A1 * | 7/2007 | Miyamoto et al. | 600/106 |
| 2008/0146873 A1 * | 6/2008 | Adams et al. | 600/104 |
| 2008/0208001 A1 * | 8/2008 | Hadani | 600/128 |
| 2008/0287961 A1 * | 11/2008 | Miyamoto et al. | 606/127 |

FOREIGN PATENT DOCUMENTS

| | | |
|---|---|---|
| JP | 2000-237121 A | 9/2000 |
| JP | 2000-325303 A | 11/2000 |
| JP | 2005-95590 A | 4/2005 |
| WO | WO 2007/026815 A | 3/2007 |

OTHER PUBLICATIONS

Japanese Office Action dated Jul. 24, 2012 (and English translation thereof) in counterpart Japanese Application No. 2007-338343.

* cited by examiner

ENDOSCOPE MAIN BODY AND ENDOSCOPE

CROSS-REFERENCE TO RELATED APPLICATIONS

This application claims the benefit of U.S. Provisional Application No. 61/009,703, filed Dec. 31, 2007.

This application is based upon and claims the benefit of priority from prior Japanese Patent Application No. 2007-338343, filed Dec. 27, 2007, the entire contents of which are incorporated herein by reference.

BACKGROUND OF THE INVENTION

1. Field of the Invention

The present invention relates to an endoscope main body constituting an endoscope in a state in which an elongated detachable observation optical system is attached to the endoscope main body, and the endoscope.

2. Description of the Related Art

As disclosed in, e.g., JP-A 2000-33071 (KOKAI), insertion sections of a plurality of endoscopes are introduced into a body cavity through one over-tube to perform a procedure while observing a surgical instrument which projects from a distal end of the insertion section of the first endoscope and a surgical instrument which projects from a distal end of the insertion section of the second endoscope by using, for example, the first endoscope.

On the other hand, it is known that instead of using the plurality of endoscopes, for example, two bendable arm sections are disposed on the distal end of the insertion section of one endoscope. To bend these arm sections, two or four wires are attached to each of the arm sections, and further to bend bending portions provided on proximal ends of the arm sections, for example, two or four wires are attached thereto. Moreover, in the insertion section of the endoscope, there is disposed a channel tube which permits the surgical instrument to project from the proximal end side of the insertion section through the distal end of each arm section. Therefore, in this endoscope, the surgical instrument is led through each channel tube, whereby the distal end of the surgical instrument projects from the distal end of the arm section while arbitrarily bending the arm section, which enables the procedure disclosed in JP-A 2000-33071 (KOKAI) with one endoscope.

BRIEF SUMMARY OF THE INVENTION

According to a first aspect of the present invention, there is provided an endoscope main body constituting an endoscope in a state in which an elongated detachable observation optical system is attached to the endoscope main body. The endoscope main body includes: an insertion section, an operating section, another operating section, a wire, another wire and a branch member. The insertion section includes an arm section having at least one bending portion; a hard portion which is provided in a proximal end of the arm section and in which a distal end of the observation optical system is disposed; and another bending portion provided separately from the bending portion of the arm section. The insertion section is detachably attached to the observation optical system provided in a proximal end of the hard portion. The operating section is provided in a proximal end of the insertion section to operate the bending portion of the arm section. The another operating section is provided in the proximal end of the insertion section to operate the other bending portion separately from the operating section which operates the bending portion of the arm section. The wire is disposed in the insertion section while connecting the bending portion of the arm section to the operating section. The another wire is disposed in the insertion section while connecting the other bending portion to the other operating section and while arrayed with the wire. The branch member is provided in the proximal end of the insertion section so that the operating section and the other operating section are branched from each other and so that the wire connected to the operating section and the other wire connected to the other operating section are branched from each other. The branch member has an opening as an inlet which guides the distal end of the observation optical system to the hard portion of the insertion section.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
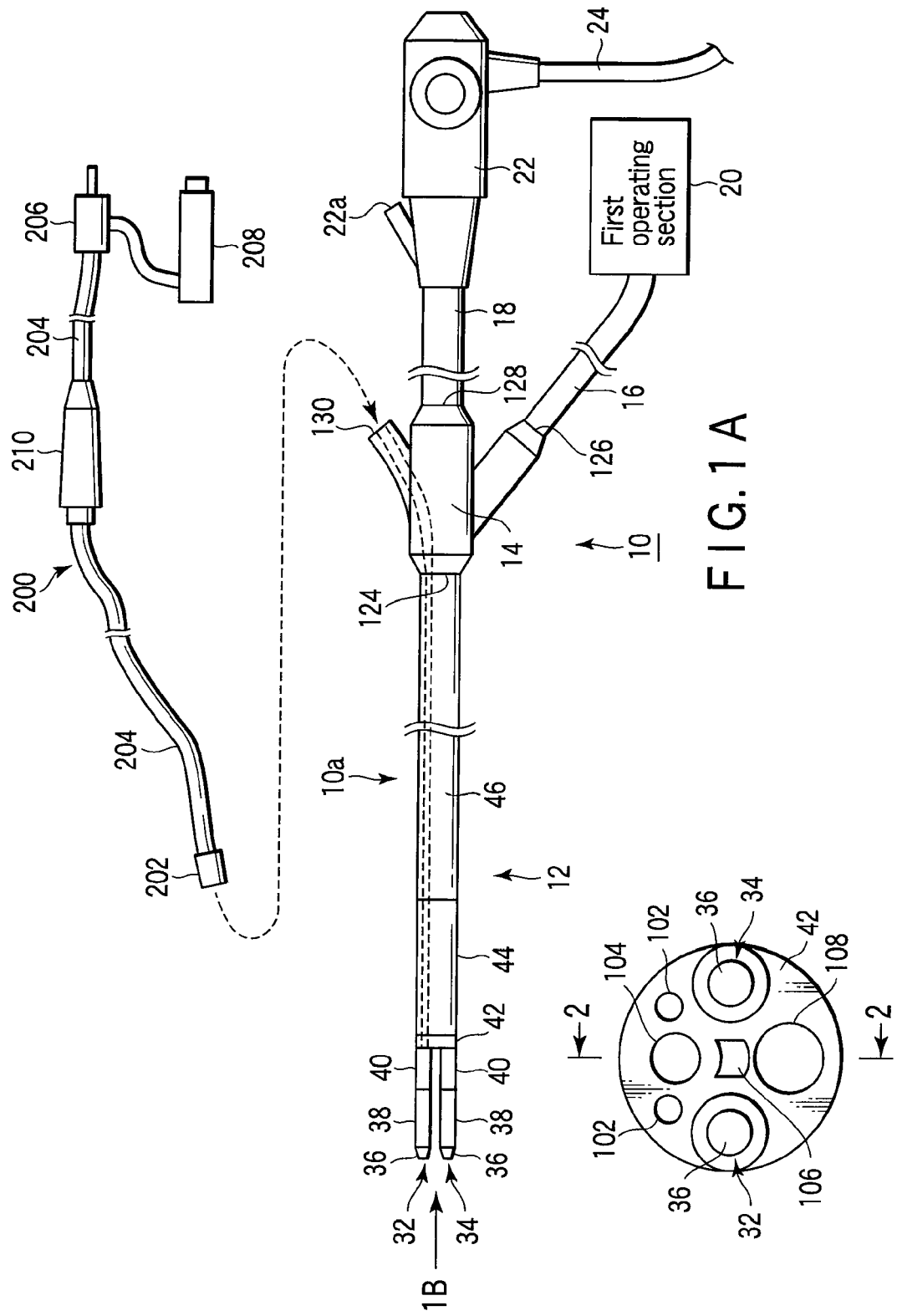
FIG. 1A is a schematic diagram showing that an observation optical system is detachable to an endoscope main body of an endoscope according to a first embodiment.
FIG. 1B is a schematic front view observed in a case where a distal end of an insertion section of the endoscope (the endoscope main body) is observed from an arrow 1B direction in FIG. 1A.

The best mode for carrying out this invention will hereinafter be described with reference to the drawings.

A first embodiment will be described with reference to FIGS. 1 to 10.

As shown in FIG. 1A, an endoscope 10 according to this embodiment includes an endoscope main body 10a and an elongate observation optical system 200.

The endoscope main body 10a includes an insertion section 12 that is inserted into a body cavity, a branch member 14 disposed in a proximal end of the insertion section 12, first and second extended sections 16 and 18 disposed on a proximal end side of the branch member 14, a first operating section (an operating section) 20 disposed in a proximal end of the first extended section 16, a second operating section (another operating section) 22 disposed in a proximal end of the second extended section 18, and a universal cord 24 extended from the second operating section 22.

The first extended section 16 having flexibility is extended from the branch member 14. The first operating section 20 bends later-explained first and second bending portions 38, 40 in each of first and second arm sections 32, 34 independently of each other. Here, the first and second bending portions 38, 40 are provided in each of the first and second arm sections 32, 34. Each of the first and second bending portions 38, 40 independently bends of each other by using later-explained wires 72, 74. Moreover, the first operating section 20 is provided with a forceps opening (not shown) that serves as an inlet through which a surgical instrument (not shown) is inserted into later-explained first and second channel tubes 62, 64. It is to be noted that each forceps opening is provided with respect to each of the first and second channel tubes 62, 64.

The second extended section 18 having flexibility is extended from the branch member 14. The second operating section 22 bends a later-explained third bending portion 44. Moreover, the second operating section 22 is provided with a forceps opening 22a that serves as an inlet through which a surgical instrument (not shown) is inserted into a later-explained third channel tube 66. The forceps opening 22a is disposed in a position deviating from the axial direction of the second extended section 18.

It is to be noted that the second extended section 18 and the second operating section 22 are coaxially disposed with a central axis of the insertion section 12 by the branch member 14. During a procedure, for example, the proximal end of the insertion section 12 or the second extended section 18 is sometimes rotated on their axis, and at this time, a force for rotating the proximal end of the insertion section 12 or the second extended section 18 can easily be transmitted to a distal end of the insertion section 12 as compared with a case where the second operating section is not coaxially disposed. That is, since the second extended section 18 and the second operating section 22 are disposed coaxially with the central axis of the insertion section 12 by the branch member 14, operability when using the endoscope 10 can satisfactorily be maintained.

The insertion section 12 includes the first and second arm sections 32, 34 each having a first hard portion (a distal end hard portion) 36 and the first and second bending portions (the bending portions) 38, 40, a second hard portion 42 disposed in proximal ends of these arm sections 32, 34, the third bending portion (the other bending portion) 44 disposed in a proximal end of the second hard portion 42, and a flexible tube portion 46 disposed in a proximal end of the third bending portion 44.

Here, the first bending portion 38 in the first to third bending portions 38, 40 and 44 is placed on the most distal end side of the insertion section 12, and the second bending portion 40 is disposed in the proximal end of the first bending portion 38. It is herein described that each of the arm sections 32, 34 has the first and second bending portions 38, 40, but, for example, a simple flexible tube (a corrugated tube) is preferably disposed between the first bending portion 38 and the second bending portion 40 or between the second bending portion 40 and the second hard portion 42.

Figure 2:
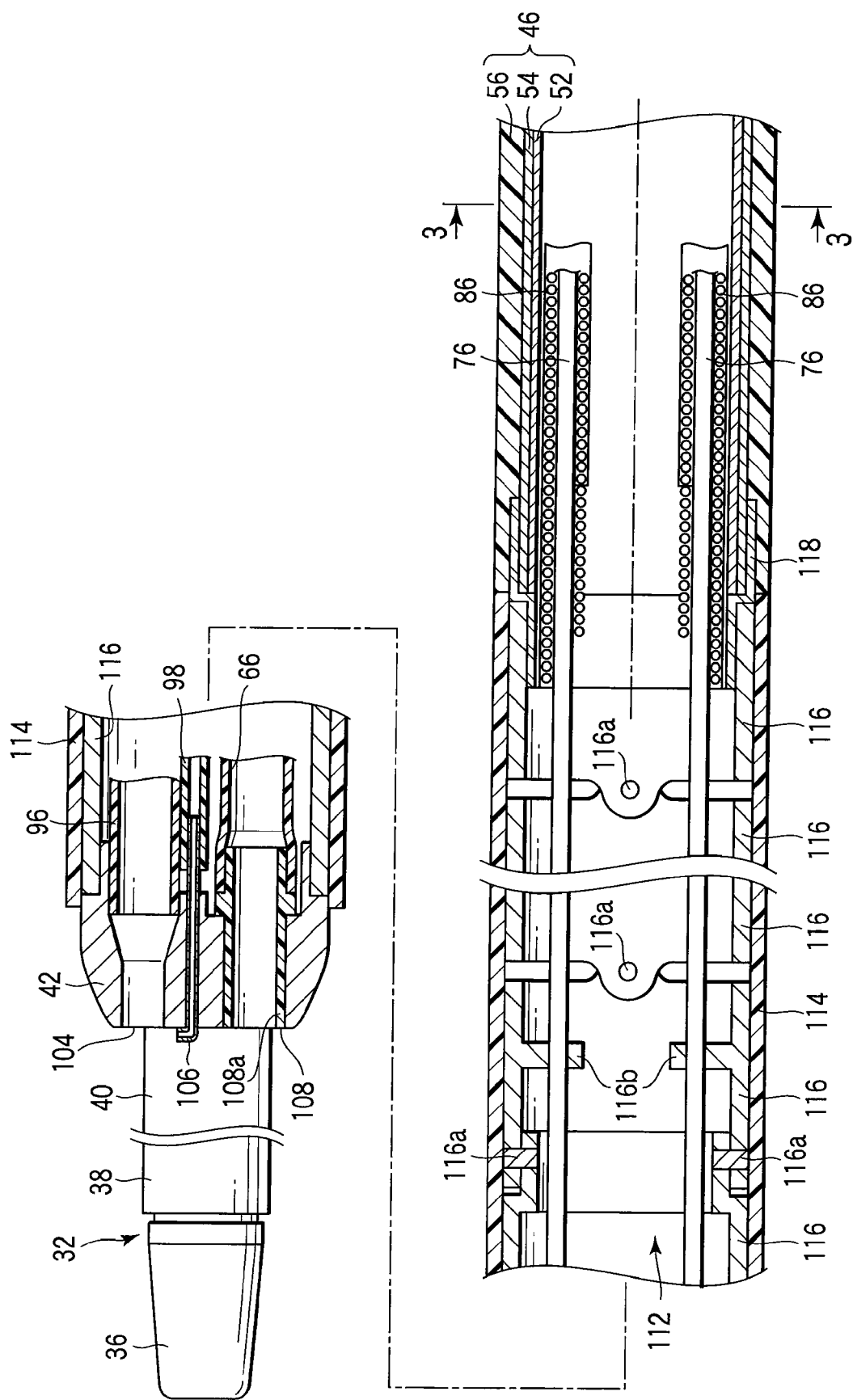
FIG. 2 is a schematic vertical cross-sectional view along line 2-2 of FIG. 1B and showing the insertion section of the endoscope main body of the endoscope according to the first embodiment.

As shown in FIG. 2, the flexible tube portion 46 of the insertion section 12 includes a helical tube 52, a mesh-like blade 54 disposed on an outer side of the helical tube 52, and an outer tube 56 disposed on an outer side of the blade 54. The helical tube 52 is formed into a substantially cylindrical shape by spirally winding, for example, a strip-like thin-plate material of stainless steel. The blade 54 is formed into a substantially cylindrical shape by combining wire bundles each obtained by bundling, for example, a plurality of stainless steel wires. The outer tube 56 is formed into a substantially cylindrical shape to cover the outer side of the blade 54 with a resin material having flexibility, for example, a rubber material.

Figure 3:
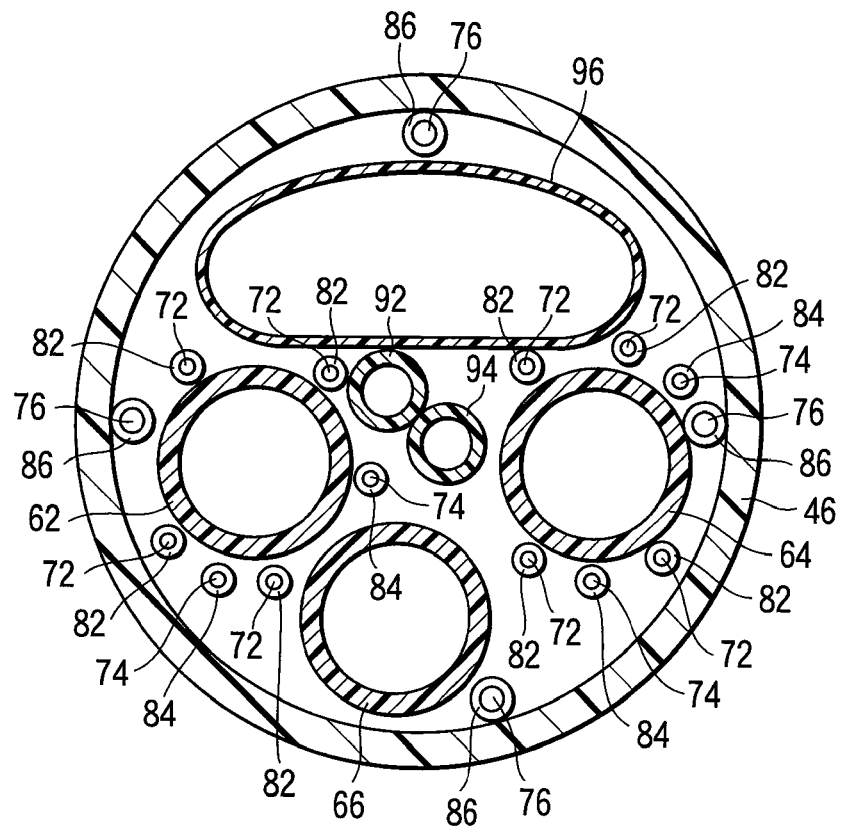
FIG. 3 is a schematic lateral cross-sectional view along line 3-3 of FIG. 2 and showing a flexible tube portion of the insertion section in the endoscope main body of the endoscope according to the first embodiment.

Moreover, as shown in FIG. 3, on an inner side of the helical tube 52 of the flexible tube portion 46 in the insertion section 12 are arranged internal members such as first to third channel tubes 62, 64 and 66, at least a pair of first wires 72, at least a pair of second wires 74, at least a pair of third wires 76, coil-like first to third wire guides 82, 84 and 86 that respectively cover the first to third wires 72, 74 and 76, an air supply tube 92, a water supply tube 94, and a guide tube (a tubular path) 96. Among them, the first to third channel tubes 62, 64 and 66, the air supply tube 92, the water supply tube 94 and the guide tube 96 are preferably formed of a fluorine-based resin material such as polytetrafluoroethylene (PTFE) or fluorinated ethylene propylene (FEP) or a polyolefin-based resin material.

The distal end of the first channel tube 62 is connected to the first hard portion 36 of the first arm section 32, and the proximal end of the same is connected to a forceps opening (not shown) of the first operating section 20 through the first and second bending portions 38, 40 of the first arm section 32, the second hard portion 42, the third bending portion 44, the flexible tube portion 46, the branch member 14 and the first extended section 16. In consequence, the unshown surgical instrument can project from the forceps opening of the first operating section 20 through the first hard portion 36 of the first arm section 32. Likewise, the distal end of the second channel tube 64 is connected to the first hard portion 36 of the second arm section 34, and the proximal end of the same is connected to a forceps opening (not shown) of the first operating section 20 through the first and second bending portions 38 and 40 of the second arm section 34, the second hard portion 42, the third bending portion 44, the flexible tube portion 46, the branch member 14 and the first extended section 16. In consequence, the unshown surgical instrument can project from the forceps opening of the first operating section 20 through the first hard portion 36 of the second arm section 34.

On the other hand, the distal end of the third channel tube 66 is connected to a relay tube 108a disposed in a later-explained distal end opening 108 of the second hard portion 42 in the proximal ends of the arm sections 32, 34, and the proximal end of the same is connected to the forceps opening 22a of the second operating section 22 through the third bending portion 44, the flexible tube portion 46, the branch member 14 and the second extended section 18. In consequence, the unshown surgical instrument can project from the forceps opening 22a of the second operating section 22 through the distal end opening 108 of the second hard portion 42.

A distal end of each first wire (the wire) 72 is connected to the distal end side portion of the first bending portion 38 of each of the first and second arm sections 32, 34, and a proximal end of the same is connected to the first operating section 20 through the second bending portion 40, the second hard portion 42, the third bending portion 44, the flexible tube portion 46, the branch member 14 and the first extended section 16. Likewise, a distal end of each second wire (the wire) 74 is connected to a distal end side portion of the second bending portion 40 of each of the first and second arm sections 32, 34, and a proximal end of the same is connected to the first operating section 20 through the second hard portion 42, the third bending portion 44, the flexible tube portion 46, the branch member 14 and the first extended section 16. In consequence, when the first operating section 20 is operated, the first and second bending portions 38, 40 of the arm sections 32, 34 are bent, respectively.

It is to be noted that in this embodiment, the first bending portions 38 provided in the first and second arm sections 32, 34 are not discriminated from each other in the above explanation for simplification, but needless to say, the first bending portions 38 can be independently and respectively bent in the first arm section 32 and the second arm section 34. This also applies to the second bending portions 40 provided in the first and second arm sections 32, 34.

Furthermore, a distal end of each first wire guide 82 is connected to the proximal end of the first bending portion 38 in each of the first and second arm sections 32 and 34, and a proximal end of the same is led through the second bending portion 40, the second hard portion 42, the third bending portion 44, the flexible tube portion 46 and the branch member 14 and extended to the inside of the first extended section 16 or the first operating section 20. Likewise, a distal end of each second wire guide 84 is connected to the proximal end of the second bending portion 40 in each of the first and second arm sections 32 and 34, and a proximal end of the same is led through the second hard portion 42, the third bending portion 44, the flexible tube portion 46 and the branch member 14 and extended to the inside of the first extended section 16 or the first operating section 20. The proximal ends of the first and second wire guides 82 and 84 do not have to be necessarily fixed.

On the other hand, a distal end of each third wire (the other wire) 76 in FIG. 2 showing only one of two pairs of third wires 76 is connected to a distal end side portion of the third bending portion 44, and a proximal end of the same is connected to the second operating section 22 through the flexible tube portion 46 and the branch member 14. A distal end of each third wire guide 86 in FIG. 2 showing only one of two pairs of third wire guides 86 is connected to the proximal end of the third bending portion 44, and a proximal end of the same is led through the flexible tube portion 46 and the branch member 14 and extended to the inside of the second extended section 18 or the second operating section 22. It is to be noted that the first to third wire guides 82, 84 and 86 are formed into, for example, a coil-like shape.

Moreover, distal ends of the air supply tube 92 and the water supply tube 94 united as an air/water supply tube denoted with reference numeral 98 (see FIG. 2) near the second hard portion 42 are connected to the second hard portion 42, and a proximal end of the air/water supply tube is branched into the air supply tube 92 and the water supply tube 94, and led through the third bending portion 44, the flexible tube portion 46, the branch member 14, the second extended section 18 and the second operating section 22 to extend to the inside of the universal cord 24. Moreover, the air supply tube 92 and the water supply tube 94 are connected to unshown connectors at the end of the universal cord 24, respectively. It is to be noted that the distal end of the air/water supply tube 98 in which the air supply tube 92 and the water supply tube 94 are put together is connected to a later-explained air supply/water supply nozzle 106.

Moreover, a distal end of the guide tube 96 is connected to the second hard portion 42, or disposed in a free state near the second hard portion 42 (see FIG. 2), and a proximal end of the same is connected to a later-explained separation plate 144 provided in the branch member 14 through the third bending portion 44 and the flexible tube portion 46. The guide tube 96 guides the observation optical system 200 from the branch member 14 to the second hard portion 42 of the insertion section 12.

As shown in FIG. 1B, in the distal end surface of the second hard portion 42 are formed a pair of illumination windows 102, an opening 104 in which a later-explained imaging section 226 of an imaging module 202 of the observation optical system 200 is disposed, the air supply/water supply nozzle 106, and the distal end opening 108 of the third channel tube 66. In this second hard portion 42, the proximal ends of the first and second arm sections 32, 34 are further disposed.

The back surface side of the distal end surface of the second hard portion 42 is provided with a recessed portion (not shown) in which the later-explained imaging module 202 of the observation optical system 200 is detachably disposed. The recessed portion is connected to the distal end of the guide tube 96. Moreover, the back surface side of the distal end surface of the second hard portion 42 is connected to the distal end of the third channel tube 66 and the distal end of the air/water supply tube 98 in which the air supply tube 92 and the water supply tube 94 are put together.

Furthermore, as shown in FIG. 2, the third bending portion 44 is provided with a bending tube 112 and an outer tube 114 so that the third bending portion can bend in, for example, four directions. It is to be noted that a blade (a mesh-like tube) may be disposed between the bending tube 112 and the outer tube 114.

In the bending tube 112, a plurality of bending pieces 116 are coupled to one another via pins 116a. The most distal end of the bending tube 112 is fixed to the second hard portion 42 by, for example, an adhesive. Furthermore, a connection mouth ring 118 is arranged between the most proximal end of the bending tube 112 and the distal end of the flexible tube portion 46. Moreover, the distal end of each third wire guide 86 is fixed to the inner peripheral surface of the connection mouth ring 118, and each third wire 76 is extended along the surface. It is to be noted that the third wires 76 are disposed on wire receiving portions 116b provided on the inner peripheral surfaces of the respective bending pieces 116. Furthermore, each third wire 76 is fixed to the distal end of the bending tube 112 (the bending piece 116 placed at the most distal end). In consequence, when each third wire 76 moves in the axial direction thereof, the third bending portion 44 bends.

Although not described in detail, the first and second bending portions 38, 40 have a structure similar to that of the third bending portion 44. Moreover, the second bending portion 40 is preferably bent only in two directions instead of four directions (see FIG. 3).

Figure 4A:
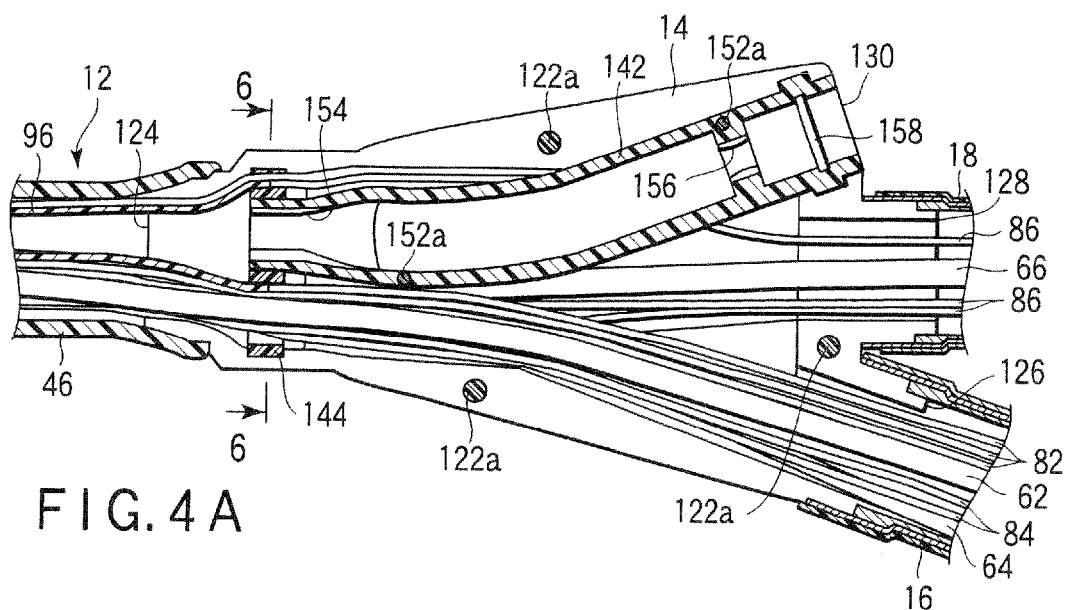
FIG. 4A is a schematic vertical cross-sectional view along line 4A-4A of FIG. 4B and showing a branch member of the endoscope main body of the endoscope according to the first embodiment.
Figure 5A:
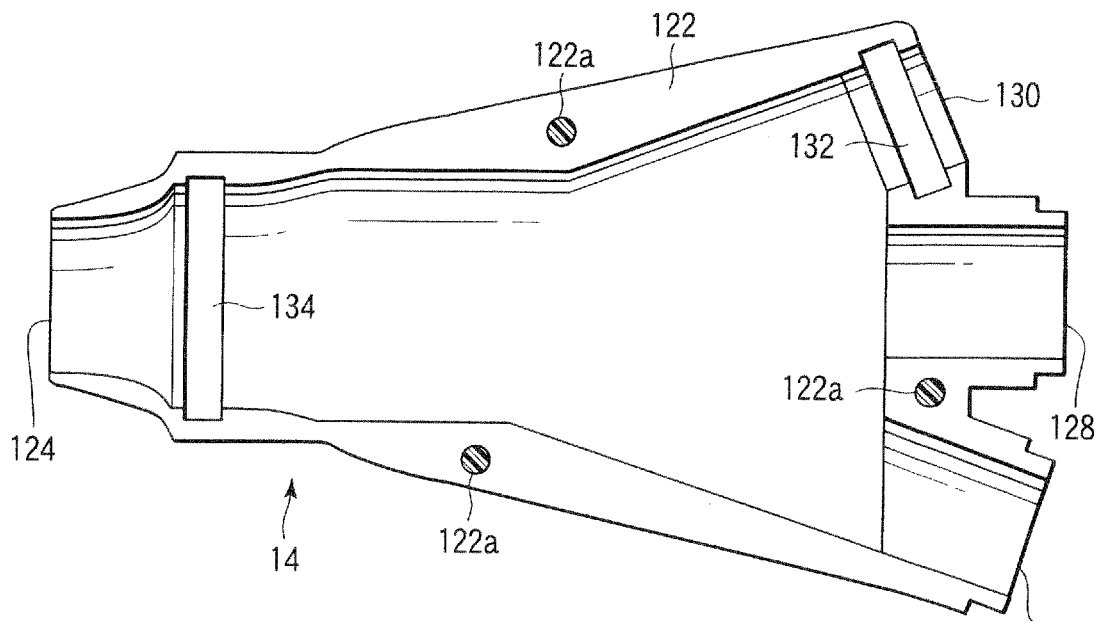
FIG. 5A is a schematic diagram showing one member of two dividable branch members in the endoscope main body of the endoscope according to the first embodiment.

As shown in FIGS. 4A and 5A, the branch member 14 includes a pair of main bodies 122, a distal end opening 124 in which the proximal end of the insertion section 12 is disposed, a first opening 126 in which the first extended section 16 is disposed, a second opening 128 in which the second extended section 18 is disposed, and a third opening 130 as an inlet through which the observation optical system 200 is detachably disposed. The first to third openings 126, 128 and 130 are connected to the distal end opening 124, respectively. The proximal end of the flexible tube portion 46 of the insertion section 12 is fixed in the distal end opening 124. The distal end of the first extended section 16 is fixed in the first opening 126. The distal end of the second extended section 18 is fixed in the second opening 128.

The main body 122 of the branch member 14 is provided with a guide member disposing portion 132 in which a later-explained guide member 142 is disposed, and a separation plate disposing portion 134 in which the separation plate 144 is disposed.

The main body 122 of the branch member 14 is formed in a state in which the main body is divided into, for example, two bodies. One of the main bodies 122 of the branch member 14 is provided with a protruding portion denoted with reference numeral 122a in FIG. 5A. The other main body 122 is provided with an unshown concave portion into which the protruding portion 122a can fit. In consequence, the one main body and the other main body of the branch member 14 can easily detachably be attached to each other.

As shown in FIG. 4A, the branch member 14 is provided with a cylindrical guide member 142 that guides the observation optical system 200, and the separation plate (the separation member) 144 disposed in the distal end of the guide member 142. The guide member 142 is detachably attached to the separation plate 144. Moreover, the guide member 142 and the separation plate 144 are detachably attached to the branch member 14.

Figure 4B:
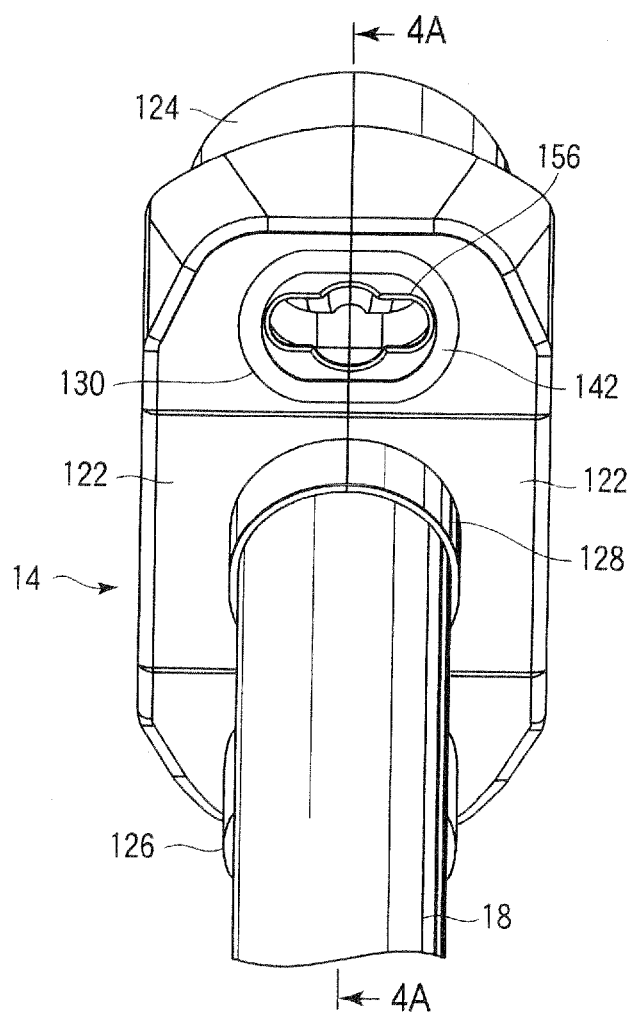
FIG. 4B is a schematic diagram showing the branch member of the endoscope main body of the endoscope in a state in which the branch member is observed from the side of a third opening.
Figures 5B, 5C:
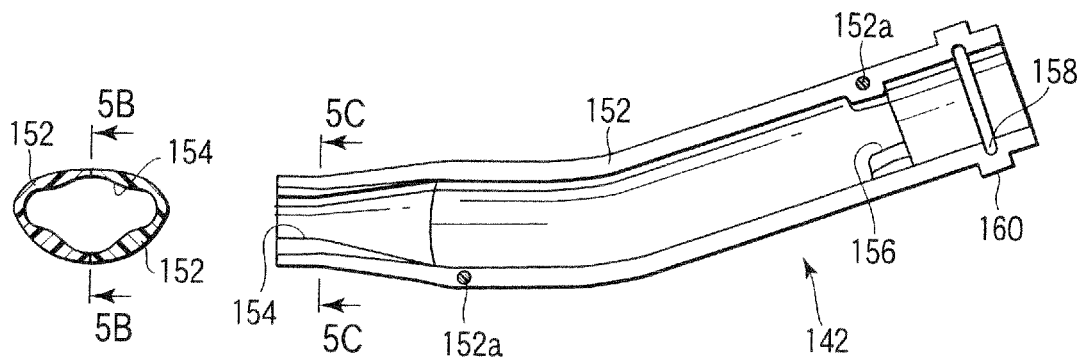
FIG. 5B is a schematic diagram along line 5B-5B of FIG. 5C and showing one member of two dividable guide members which can be disposed in the branch member of the endoscope main body of the endoscope.
FIG. 5C is a schematic lateral cross-sectional view along line 5C-5C of FIG. 5B.

The guide member 142 is disposed between the distal end opening 124 of the branch member 14 and the third opening 130. Moreover, as shown in FIGS. 5B and 5C, the guide member 142 includes a pair of main bodies 152. Moreover, a first narrow portion (a direction regulating portion) 154 is formed in the inner peripheral surface of the distal end of the guide member 142, and as shown in FIGS. 4B and 5B, a second narrow portion (a direction regulating portion) 156 is formed in the inner peripheral surface of the proximal end of the guide member 142. Furthermore, the inner peripheral surface of the second narrow portion 156 on a further proximal end side is provided with a groove-like engagement target portion 158 with which an engagement portion 246 of a later-explained protection hood 210 of the observation optical system 200 is detachably engaged. On the other hand, the outer peripheral surface of the second narrow portion 156 on a further proximal end side is provided with a flange portion 160 disposed in the guide member disposing portion 132 of the branch member 14.

As shown in FIG. 5C, the first narrow portion 154 has substantially the same shape as that of the later-explained imaging module 202 of the observation optical system 200, and is formed to be slightly larger than the imaging module 202. Moreover, the second narrow portion 156 has substantially the same outer shape as that of the imaging module 202, and is formed to be slightly larger than the first narrow portion 154.

It is to be noted that the main body 152 of the guide member 142 is preferably formed in a state in which the main body is divided into, for example, two bodies. One of the main bodies 152 of the guide member 142 is provided with a protruding portion denoted with reference numeral 152a in FIG. 5B. The other main body 152 of the guide member 142 is provided with an unshown concave portion into which the protruding portion 152a can fit. In consequence, the one main body and the other main body of the guide member 142 can easily detachably be attached to each other.

When the branch member 14 is dividable into two main bodies, the separation plate 144 may integrally be formed in one of a pair of main bodies 122 of the branch member 14, or the separation plate 144 may detachably be attached to the branch member 14.

Figure 5D:
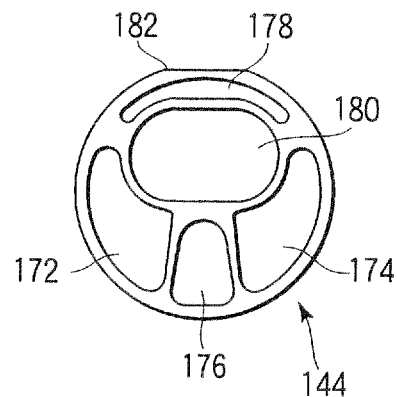
FIG. 5D is a schematic front view showing a separation plate disposed in the branch member of the endoscope main body of the endoscope.

The separation plate 144 is disposed in the vicinity of the distal end opening 124 of the branch member 14. The separation plate 144 is formed into a substantially disc-like shape. Moreover, as shown in FIG. 5D, the separation plate 144 includes first to fifth regions 172, 174, 176, 178 and 180 opened, respectively. Furthermore, an upper portion of the separation plate 144 in FIG. 5D is formed into a flat surface 182 so that the separation plate is prevented from being rotated around its axis to specify the direction of the plate.

Figure 6:
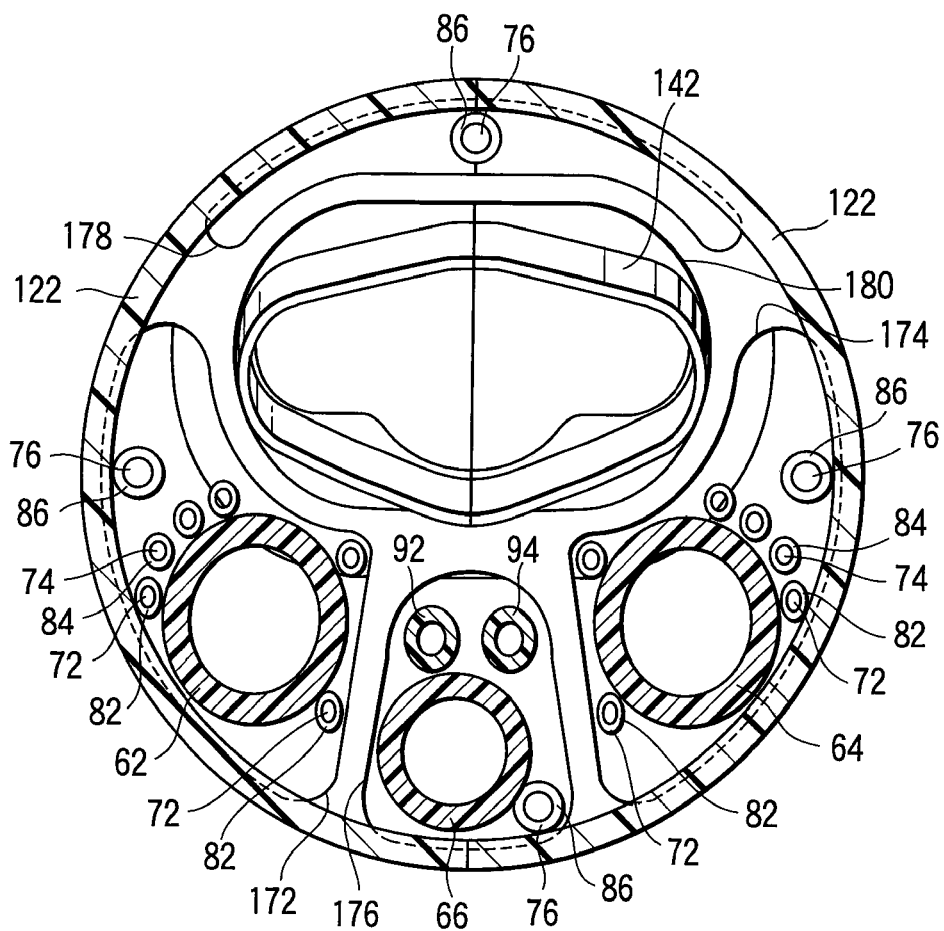
FIG. 6 is a schematic lateral cross-sectional view along line 6-6 of FIG. 4A and showing the branch member provided in a proximal end of the insertion section in the endoscope main body of the endoscope according to the first embodiment.

As shown in FIG. 6, in the first region 172, the first channel tube 62 is inserted so that the distal end of the tube 62 is disposed in the first hard portion 36 of the first arm section 32, and the first and second wires 72, 74 that bend the bending portions 38, 40 of the first arm section 32 and the first and second wire guides 82, 84 covering these wires 72, 74 are also inserted.

In the second region 174, the second channel tube 64 is inserted so that the distal end of the tube 64 is disposed in the first hard portion 36 of the second arm section 34, and the first and second wires 72, 74 that bend the first and second bending portions 38, 40 of the second arm section 34 and the first and second wire guides 82, 84 that cover these wires 72, 74 are inserted.

In the third region 176, the third channel tube 66 is inserted so that the distal end of the tube 66 is disposed in the second hard portion 42, and the air supply tube 92 and the water supply tube 94 are inserted.

Moreover, in the first to fourth regions 172, 174, 176 and 178, the third wires 76 that bend the third bending portion 44 and the third wire guides 86 covering these wires 76 are disposed.

The fifth region 180 is connected to the distal end of the above-explained guide member 142 and the proximal end of the above guide tube 96.

In the endoscope main body 10a, the observation optical system 200 is detachably disposed in consideration of cleaning properties. That is, the observation optical system 200 can be detached from the endoscope main body 10a, and hence the observation optical system 200 can easily be cleaned, disinfected and sterilized as compared with a case where the observation optical system is incorporated in the endoscope (not shown).

As shown in FIG. 1A, the observation optical system 200 includes the imaging module 202, cable units 204, a light guide connector 206, an imaging connector 208 and the protection hood 210.

Figures 7A, 7B:
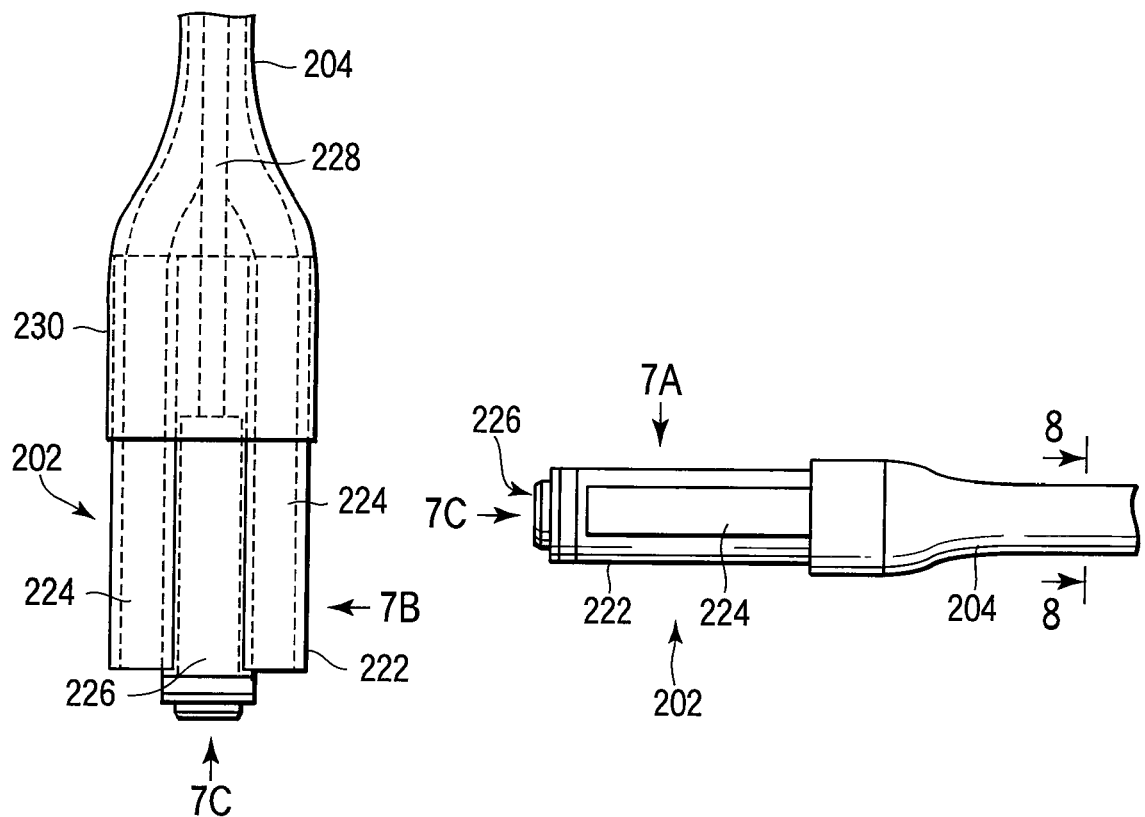
FIG. 7A is a top plan view schematically showing a distal end of the observation optical system detachably attached to the endoscope main body of the endoscope according to the first embodiment.
FIG. 7B is a side view schematically showing the distal end of the observation optical system detachably attached to the endoscope main body of the endoscope according to the first embodiment.
Figure 7C:
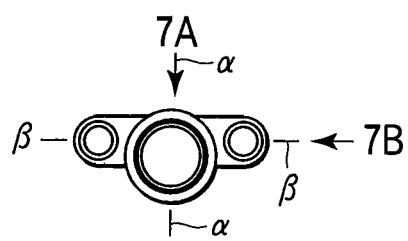
FIG. 7C is a front view schematically showing the distal end of the observation optical system detachably attached to the endoscope main body of the endoscope according to the first embodiment.

As shown in FIGS. 7A to 7C, the imaging module 202 emits illuminative light to a target (a subject), and images an observation image obtained by the illuminative light. Moreover, the imaging module 202 is detachably disposed on the back surface side of the second hard portion 42 of the insertion section 12.

The imaging module 202 includes a casing 222 formed of, for example, a metal material. As shown in FIG. 7A, in this casing 222, a pair of light guide bundles 224 for emitting the illuminative light, and the imaging section (including an objective optical system) 226 that images the observation image are disposed. In particular, the imaging section 226 is disposed between the pair of light guide bundles 224. Moreover, proximal ends of the light guide bundles 224 are connected to the light guide connector 206. Moreover, a proximal end of the imaging section 226 disposed in the casing 222 is connected to a signal line 228. A proximal end of the signal line 228 is connected to the imaging connector 208.

The casing 222 is formed symmetrically with respect to line α-α of FIG. 7C, but is formed asymmetrically with respect to line β-β thereof. That is, the casing 222 has a direction. In this case, the central axis of the imaging section 226 is disposed on line α-α of FIG. 7C, and the centers of the light guide bundles 224 are disposed in positions placed as much as an equal distance away from the central axis of the imaging section 226. In consequence, the casing 222 is formed symmetrically with respect to line α-α of FIG. 7C. On the other hand, the central axis of the light guide bundles 224 is disposed on line β-β and the central axis of the imaging section 226 is positioned away from line β-β. That is, the imaging module 202 in the distal end of the observation optical system 200 includes a portion formed asymmetrically with respect to an axis (line β-β in this embodiment) in a plane crossing the longitudinal direction of the observation optical system 200 (the longitudinal direction of the cable unit 204) at right angles. In consequence, the casing 222 is formed asymmetrically with respect to line β-β of FIG. 7C.

The direction of the imaging module 202 of the observation optical system 200 is regulated in this manner. Therefore, when the observation optical system 200 is disposed in the insertion section 12 of the endoscope main body 10a by appearance, touch or the like of the imaging module 202, the direction of the imaging module 202 with respect to the third opening 130 of the branch member 14 can easily be judged.

It is to be noted that in this embodiment, it has been described above that the casing 222 is formed symmetrically with respect to line α-α, but the casing is preferably asymmetric with respect to line α-α.

Figure 8:
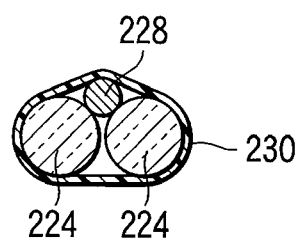
FIG. 8 is a schematic lateral cross-sectional view along line 8-8 of FIG. 7B and showing a cable unit of the observation optical system detachably attached to the endoscope main body of the endoscope according to the first embodiment.

As shown in FIG. 8, the cable unit 204 is formed into a cable-like shape in which the later-explained pair of light guide bundles 224 and the signal line 228 are integrated by a thermally shrinkable tube 230. Moreover, as shown in FIGS. 1A and 9, the protection hood 210 is disposed on the outer side of the cable unit 204.

Figure 9:
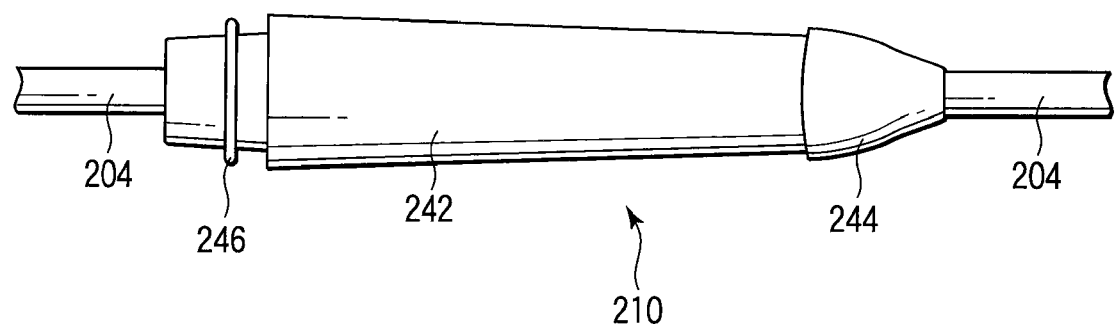
FIG. 9 is a schematic diagram showing a protection hood disposed outside the cable unit of the observation optical system detachably attached to the endoscope main body of the endoscope according to the first embodiment.

As shown in FIG. 9, the protection hood 210 includes a hard cylindrical main body 242 formed of a resin material, a rubber material, an elastomer material or the like, and a thermally shrinkable tube 244 disposed in a proximal end of the main body 242 to integrate the main body 242 and the cable unit 204. A distal end of the main body 242 of the protection hood 210 is formed into a pipe-like shape having a small diameter so that the distal end is disposed in the proximal end of the second narrow portion 156 of the guide member 142 disposed in the third opening 130 of the branch member 14. Moreover, the outer peripheral surface of the distal end of the main body 242 of the protection hood 210 is provided with the engagement portion 246 detachably engaged with the engagement target portion 158 of the guide member 142 disposed in the third opening 130 of the branch member 14. At this time, the imaging module 202 of the observation optical system 200 is disposed in the second hard portion 42 of the insertion section 12.

It is to be noted that for the protection hood 210, instead of or in addition to the above thermally shrinkable tube 244, a protective member such as a tube may be disposed on the outer periphery of the cable unit 204, and the protective member may be fixed to the inner peripheral surface of the main body 242 with an adhesive or the like.

Moreover, the light guide connector 206 is detachably connected to an unshown light source, and the illuminative light is supplied so that the illuminative light is guided from the proximal ends (incidence ends) of the light guide bundles 224 to the distal ends (exit ends) thereof. The imaging connector 208 is detachably connected to a camera control unit (not shown) connected to an unshown monitor, and the observation image imaged by the imaging section 226 is displayed in the monitor via the signal line 228 and the camera control unit.

Next, a function of the endoscope 10 according to this embodiment will be described.

When using the endoscope 10, the imaging module 202 of the observation optical system 200 is inserted into the third opening 130 of the branch member 14 of the endoscope main body 10a. In the third opening 130 of the branch member 14, the second narrow portion 156 of the guide member 142 is disposed. In consequence, when the imaging module 202 has a predetermined direction, the imaging module 202 can be passed through the second narrow portion 156 of the guide member 142. That is, when the second narrow portion 156 has a state shown in, for example, FIG. 4B, the imaging module 202 of the observation optical system 200 having a state shown in FIG. 7C passes through the second narrow portion 156.

On the other hand, when the imaging module 202 has a direction other than the predetermined direction, the imaging module 202 cannot be passed through the second narrow portion 156 of the guide member 142. That is, when the second narrow portion 156 has the state shown in, for example, FIG. 4B and the imaging module 202 is inverted as much as 180 degrees around the axis of the cable unit 204 with respect to the state of the observation optical system 200 shown in FIG. 7C, the distal end of the imaging module abuts on the proximal end of the second narrow portion 156, and cannot extend through the second narrow portion 156. Therefore, in a case where it is judged whether or not the imaging module 202 of the observation optical system 200 can be passed through the second narrow portion 156 of the guide member 142, when the observation optical system 200 is inserted into the insertion section 12, it can be recognized whether or not the imaging module 202 has a correct direction. Therefore, when the imaging module 202 of the observation optical system 200 cannot be passed through the second narrow portion 156, an attempt is made to invert the imaging module 202 as much as 180 degrees around the axis of the cable unit 204 and pass the module through the second narrow portion 156.

When the imaging module 202 of the observation optical system 200 can be passed through the second narrow portion 156 of the guide member 142, further for confirmation, the imaging module 202 is passed through the first narrow portion 154. At this time, when the imaging module 202 of the observation optical system 200 has a predetermined direction (e.g., the state shown in FIG. 7C), the imaging module 202 can be passed through the first narrow portion 154 of the guide member 142.

On the other hand, when the imaging module 202 has a direction other than the predetermined direction (e.g., a state in which the module is inverted as much as 180 degrees with respect to the state shown in FIG. 7C), the imaging module 202 cannot be passed through the first narrow portion 154 of the guide member 142. It is to be noted that there are some cases where the imaging module 202 can be passed through the second narrow portion 156, and the imaging module 202 cannot be passed through the first narrow portion 154, because the second narrow portion 156 is formed to have an opening portion larger than that of the first narrow portion 154. Therefore, in a case where it is judged whether or not the imaging module 202 of the observation optical system 200 can be passed through the first narrow portion 154 of the guide member 142, when the observation optical system 200 is inserted into the insertion section 12, it can be recognized whether or not the imaging module 202 has a correct direction.

It is to be noted that a space larger than the narrow portion 156 or 154 is formed between the second narrow portion 156 and the first narrow portion 154, but the imaging module 202 cannot be rotated or inverted in such a space. Therefore, when the imaging module 202 cannot be passed through the first narrow portion 154 of the guide member 142, an attempt is made to once extract the imaging module 202 from the guide member 142 through the second narrow portion 156, invert the module as much as 180 degrees around the axis of the cable unit 204 and then pass the module through the second narrow portion 156. Afterward, a further attempt is made to pass the module through the first narrow portion 154.

Therefore, the imaging module 202 is passed through the guide member 142 to set the direction of the imaging module, that is, the direction of the observation optical system 200 to the predetermined direction.

Moreover, the imaging module 202 of the observation optical system 200 is guided toward the second hard portion 42 by the guide tube 96 connected to the fifth region 180 of the separation plate 144. At this time, in the flexible tube portion 46 of the insertion section 12, there are disposed internal members such as the first to third channel tubes 62, 64 and 66, at least a pair of first wires 72, at least a pair of second wires 74, at least a pair of third wires 76, the first to third wire guides 82, 84 and 86 having, for example, a coil-like shape and covering these first to third wires 72, 74 and 76, respectively, the air supply tube 92, the water supply tube 94 and the guide tube 96. In consequence, there is not any space in the guide tube 96 in which the imaging module 202 rotates around the axis of the cable unit 204 as shown in FIGS. 7A to 7C. Therefore, the imaging module 202 of the observation optical system 200 having a direction in which the module is guided by the guide member 142 is disposed in the second hard portion 42.

Figure 10:
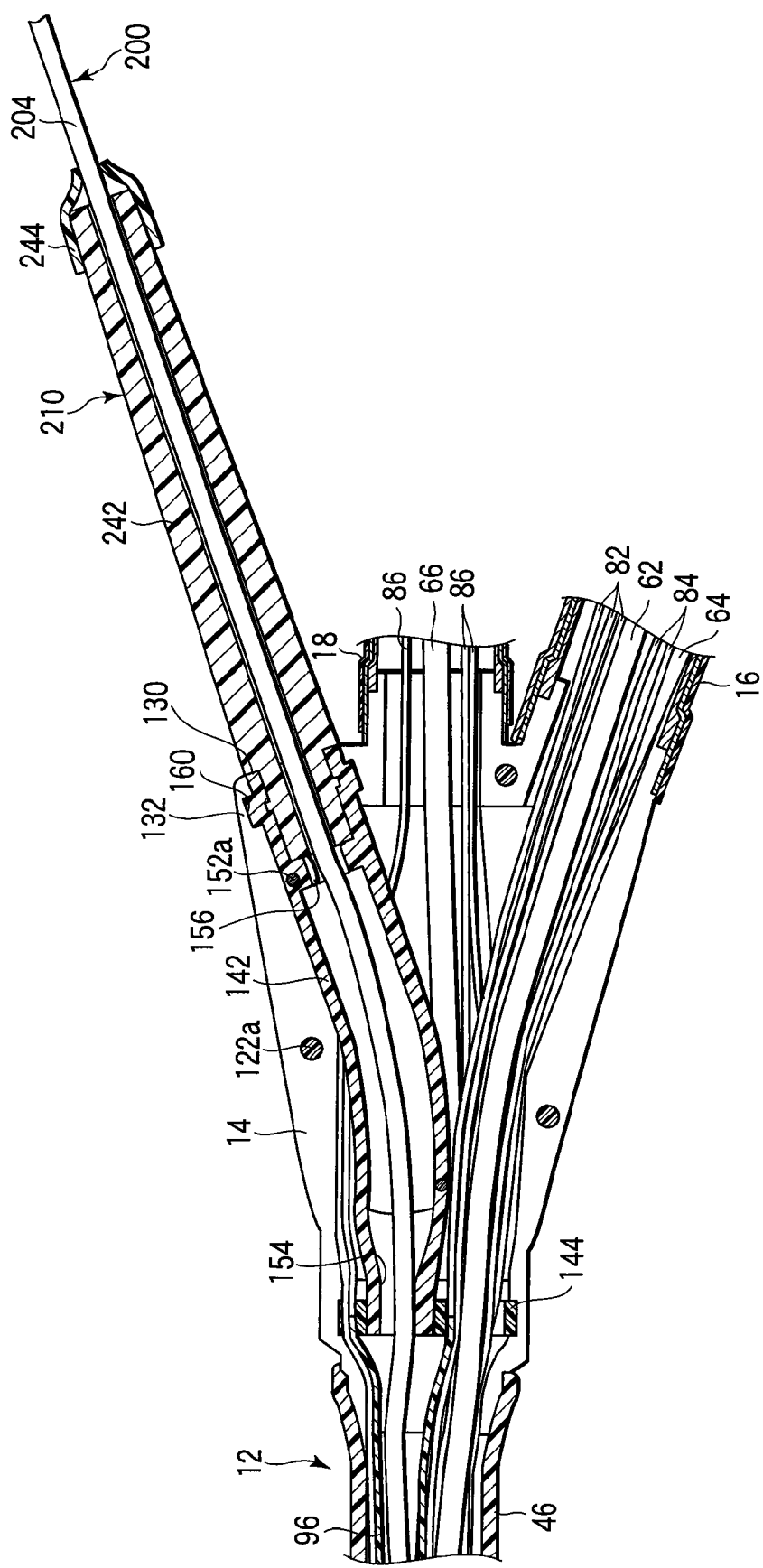
FIG. 10 is a schematic vertical cross-sectional view showing a state in which the observation optical system is disposed in the endoscope main body of the endoscope according to the first embodiment, particularly a state in which the protection hood of the observation optical system is engaged with a proximal end of the guide member disposed in the third opening of the branch member.

As described above, when the imaging module 202 of the observation optical system 200 is disposed in the second hard portion 42, as shown in FIG. 10, the engagement portion 246 at the distal end of the protection hood 210 disposed outside the cable unit 204 is engaged with the engagement target portion 158 in the proximal end of the second narrow portion 156 of the guide member 142 disposed in the third opening 130 of the branch member 14. In consequence, the observation optical system 200 is positioned with respect to the endoscope main body 10a.

The insertion section 12 of the endoscope 10 (the endoscope main body 10a) in this state is inserted into a body cavity to perform any type of procedure by operating the first and second operating sections 20, 22 to appropriately bend the first to third bending portions 38, 40 and 44, inserting an appropriate surgical instrument through the first to third channel tubes 62, 64 and 66, or discharging a gas or a solution from the air supply/water supply nozzle 106 through the air supply tube 92 and the water supply tube 94 to clean the imaging section 226 of the imaging module 202 of the observation optical system 200. Then, after ending the procedure, the insertion section 12 is removed from the body cavity.

Afterward, engagement between the engagement target portion 158 in the proximal end of the second narrow portion 156 of the guide member 142 disposed in the third opening 130 of the branch member 14 of the endoscope 10 (the endoscope main body 10a) and the engagement portion 246 of the protection hood 210 of the observation optical system 200 is released. Then, the observation optical system 200 is slowly extracted from the insertion section 12. At this time, the imaging module 202 of the observation optical system 200 is passed through the first narrow portion 154 of the guide member 142, and taken outwards through the second narrow portion 156

The endoscope main body 10a is discarded, or cleaned, disinfected and sterilized to be reused. On the other hand, the observation optical system 200 is cleaned, disinfected and sterilized to be reused.

As described above, this embodiment is as follows.

Since the branch member 14 is disposed in the proximal end of the insertion section 12 and the branch member 14 is provided with the third opening 130 for removing or inserting the imaging module 202 of the observation optical system 200, to mount the observation optical system 200 on the endoscope main body 10a, the imaging module 202 is merely inserted into the third opening 130, so that the imaging module 202 can easily be disposed in the insertion section 12. Moreover, to remove the observation optical system 200 from the endoscope main body 10a, the imaging module 202 can easily be taken out through the third opening 130. The cleaning, disinfecting and sterilizing of the endoscope main body 10a can be performed separately from the cleaning, disinfecting and sterilizing of the observation optical system 200. Moreover, when the endoscope main body 10a is discarded, the only observation optical system 200 can be cleaned, disinfected and sterilized. Therefore, for example, while the endoscope main body 10a is cleaned, disinfected and sterilized, the observation optical system 200 may be mounted on the other endoscope main body 10a to use the endoscope 10, and thus the observation optical system 200 can more efficiently be used.

Moreover, in the distal end of the branch member 14, that is, in the proximal end of the insertion section 12, the separation plate 144 is provided to array various types of the tubes 62, 64, 66, 92, 94 and 96, the wires 72, 74 and 76 and the wire guides 82, 84 and 86. In consequence, the tubes 62, 64, the wires 72, 74 and the wire guides 82, 84 extending to the first extended section 16 or the first operating section 20 can securely be separated from the tubes 66, 92 and 94, the wire 76 and the wire guide 86 extending to the second extended section 18 or the second operating section 22. Furthermore, since the separation plate 144 is provided with a space (the fifth region 180) for inserting or removing the observation optical system 200, the tubes 62, 64, 66, 92 and 94, the wires 72, 74 and 76 and the wire guides 82, 84 and 86 can easily be separated from the observation optical system 200. Therefore, the arranged internal members maintain substantially the same states from the distal ends thereof to the separation plate 144, so that the space of the guide tube 96 can securely be held by the internal members, and the imaging module 202 can easily be inserted or removed.

Moreover, since the guide member 142 that guides the observation optical system 200 is provided between the distal end opening 124 of the branch member 14 and the third opening 130, the observation optical system 200 can clearly be separated from paths for the tubes 62, 64, 66, 92 and 94, the wires 72, 74 and 76 and the wire guides 82, 84 and 86 in the branch member 14.

Furthermore, the distal end of the guide member 142 is provided with the first narrow portion 154, and the proximal end thereof is provided with the second narrow portion 156. Therefore, the imaging module 202 of the observation optical system 200 can securely be disposed in the insertion section 12 through the branch member 14 in a state in which the direction of the imaging module 202 of the observation optical system 200 is regulated.

In addition, a lateral cross-sectional area of a space of the guide member 142 between the first narrow portion 154 and the second narrow portion 156 decreases from the second narrow portion 156 to the first narrow portion 154, so that the imaging module 202 can securely be guided to the first narrow portion 154.

Moreover, since the distal end of the separation plate 144 is provided with the guide tube 96 inserted through the flexible tube portion 46 of the insertion section 12 and the third bending portion 44, the imaging module 202 which projects from the third opening 130 of the branch member 14 through the distal end opening 124 can securely be guided to the second hard portion 42.

Furthermore, the second extended section 18 and the second operating section 22 are disposed on the same axis as that of the insertion section 12 by the branch member 14. In consequence, for example, in a case where the second extended section 18 or the second operating section 22 is rotated around the axis thereof to rotate the insertion section 12 around the axis thereof, a force can easily be transmitted as compared with a case where the first extended section 16 or the first operating section 20 is rotated around the axis thereof.

Additionally, in a case where the protection hood 210 is detachably fixed to the proximal end of the guide member 142 provided in the branch member 14, the observation optical system 200 can detachably be fixed in a watertight manner in a state where the observation optical system 200 is placed in a predetermined position with respect to the endoscope main body 10a.

It is to be noted that it has been described in this embodiment that the separation plate 144 is connected to the guide tube 96 of the observation optical system 200, but the distal end of the guide member 142 may preferably be connected to the guide tube 96. Moreover, the guide tube 96 may be connected to the bending piece 116 on the most distal end side.

Moreover, in this embodiment, the first bending portion 38 can be bent in four directions, but the directions may appropriately be set to, for example, two directions. Furthermore, the direction of the first arm section 32 may be set to a direction different from that of the second arm section 34. Furthermore, the third bending portion 44 may be bent in four or two directions. In consequence, the numbers of the wires 72, 74 and 76 and the wire guides 82, 84 and 86 disposed in the flexible tube portion 46 of the insertion section 12 can be increased or decreased.

Additionally, in this embodiment, as shown in FIG. 1A, the arm sections 32, 34 have the same structure, but the lengths of the arm sections 32, 34, the amounts of the bending portions 38, 40 to be bent or the like may be set to values of the arm sections 32, 34 different from each other.

Figure 11A:
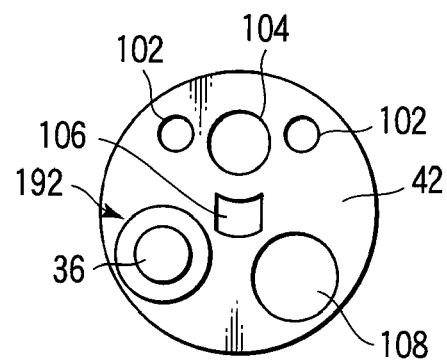
FIG. 11A is a schematic front view of a modification of the endoscope main body of the endoscope according to the first embodiment in a state in which the endoscope main body has one arm section observed in a case where a distal end of an insertion section of the endoscope (the endoscope main body) is observed from the arrow 1B direction of FIG. 1A.

Moreover, it has been described in this embodiment that two arm sections 32, 34 are disposed on the distal end side of the second hard portion 42, but as shown in FIG. 11A, it is preferable to provide only one arm section 192 having the first hard portion 36 and the first and second bending portions 38, 40 in the same manner as in the arm sections 32, 34 described in the first embodiment. Even in this case, needless to say, the first hard portion 36 of the arm section 192 is preferably provided with a distal end opening (not shown) communicating with unshown channel tubes (corresponding to the first and second channel tubes 62, 64 in the first embodiment).

Figure 11B:
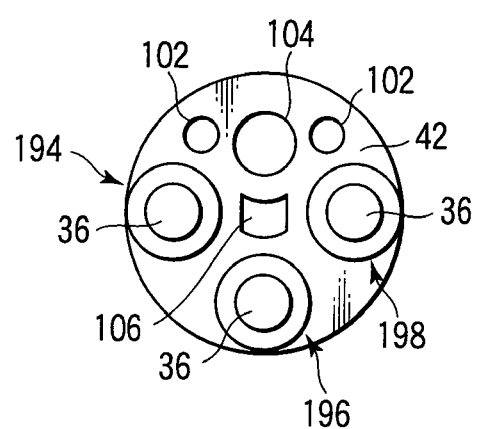
FIG. 11B is a schematic front view of the modification of the endoscope main body of the endoscope according to the first embodiment in a state in which the endoscope main body has three arm sections observed in a case where the distal end of the insertion section of the endoscope (the endoscope main body) is observed from the arrow 1B direction of FIG. 1A.

On the other hand, as shown in FIG. 11B, it is preferable to provide three arm sections 194, 196 and 198 each having the first hard portion 36 and the first and second bending portions 38, 40 in the same manner as in the arm sections 32, 34 described in the first embodiment. In this case, the distal end opening 108 may be provided as shown in FIGS. 1B and 11A, or may not be provided. Even in this case, needless to say, the first hard portion 36 of each of the respective arm sections 194, 196 and 198 is preferably provided with a distal end opening (not shown) communicating with unshown channel tubes (corresponding to the first and second channel tubes 62, 64 in the first embodiment).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope main body for use in combination with an elongated observation optical system which is attachable to and detachable from the endoscope main body, wherein the elongated observation optical system includes a distal end portion formed asymmetrically with respect to an axis in a plane crossing a longitudinal direction of the observation optical system at right angles, the endoscope main body comprising:

an insertion section including:
an arm section having at least one bending portion;
a hard portion which is provided at a proximal end of the arm section, wherein the distal end portion of the observation optical system is disposable in the hard portion; and
another bending portion provided separately from the bending portion of the arm section;
wherein the insertion section is detachably attached to the observation optical system provided at a proximal end of the hard portion;
an operating section provided at a proximal end of the insertion section to operate the bending portion of the arm section;
another operating section provided at the proximal end of the insertion section to operate the other bending portion separately from the operating section which operates the bending portion of the arm section;
a wire disposed in the insertion section and connecting the bending portion of the arm section to the operating section;
another wire disposed in the insertion section and connecting the other bending portion to the other operating section, wherein the another wire is arrayed with the wire;
a branch member which includes a connection part connected to the proximal end of the insertion section, and which is provided at the proximal end of the insertion section such that (i) the operating section and the other operating section are branched from each other and (ii) the wire connected to the operating section and the other wire connected to the other operating section are branched from each other, the branch member having an opening as an inlet which guides the distal end portion of the observation optical system to the hard portion of the insertion section; and
a guide member which is provided between the opening and the connection part of the branch member, and which guides the distal end portion of the observation optical system to be disposed in the hard portion from the opening of the branch member to the connection part;
wherein the guide member includes a direction regulating portion on at least one of a side close to the opening of the branch member and a side close to the connection part such that (i) the distal end portion of the observation optical system to be disposed in the hard portion is guided from the opening to the connection part when the distal end portion of the observation optical system has a predetermined direction and (ii) the distal end portion of the observation optical system is prevented from being guided from the opening to the connection part when the distal end portion of the observation optical system has a direction different from the predetermined direction; and
wherein the guide member is cylindrically formed, and an inner shape of the guide member is tapered along an outer shape of the distal end portion of the observation optical system from the side close to the opening of the branch member to the side close to the connection part.

2. The endoscope main body according to claim 1, further comprising a separation member which is provided in the branch member and which is configured to detachably attach the observation optical system to the insertion section while separating the wire and the other wire disposed in the insertion section from the observation optical system detachably disposed in the insertion section and while arraying the wires and the observation optical system.

3. The endoscope main body according to claim 2, wherein the separation member is connected to a tubular path disposed in the insertion section so that the distal end portion of the observation optical system is guided to the hard portion.

4. The endoscope main body according to claim 2, wherein the guide member between the side close to the opening of the branch member and a side close to the separation member provided in the branch member is configured to prevent the observation optical system from rotating about the longitudinal direction of the observation optical system.

5. The endoscope main body according to claim 1, wherein the other operating section is disposed on a same axis as an axis of the insertion section by the branch member.

6. An endoscope comprising:
the endoscope main body according to claim 1; and
the observation optical system to be inserted from the opening of the branch member of the endoscope main body.

7. The endoscope according to claim 6, wherein the distal end portion of the observation optical system comprises an imaging module disposed in the hard portion, and the observation optical system further includes a cable unit extended from a proximal end of the imaging module, and
wherein at least a part of the imaging module is formed asymmetrically with respect to the axis in the plane crossing the longitudinal direction of the observation optical system at right angles so that the direction of the imaging module with respect to the opening of the branch member is judged in a case where the imaging module is disposed in the hard portion through the opening of the branch member.

8. An endoscope comprising:
an endoscope main body; and
an elongated observation optical system which is attachable to and detachable from the endoscope main body, wherein the elongated observation optical system includes a distal end portion formed asymmetrically with respect to an axis in a plane crossing a longitudinal direction of the observation optical system at right angles;
wherein the endoscope main body comprises:
an insertion section including:
an arm section having at least one bending portion;
a hard portion which is provided at a proximal end of the arm section, wherein the distal end portion of the observation optical system is disposable in the hard portion; and
another bending portion provided separately from the bending portion of the arm section;
wherein the insertion section is detachably attached to the observation optical system provided at a proximal end of the hard portion;
an operating section provided at a proximal end of the insertion section to operate the bending portion of the arm section;
another operating section provided at the proximal end of the insertion section to operate the other bending portion separately from the operating section which operates the bending portion of the arm section;
a wire disposed in the insertion section and connecting the bending portion of the arm section to the operating section;

another wire disposed in the insertion section and connecting the other bending portion to the other operating section, wherein the another wire is arrayed with the wire;

a branch member which includes a connection part connected to the proximal end of the insertion section, and which is provided at the proximal end of the insertion section such that (i) the operating section and the other operating section are branched from each other and (ii) the wire connected to the operating section and the other wire connected to the other operating section are branched from each other, the branch member having an opening as an inlet which guides the distal end portion of the observation optical system to the hard portion of the insertion section; and a guide member which is provided between the opening and the connection part of the branch member, and which guides the distal end portion of the observation optical system to be disposed in the hard portion from the opening of the branch member to the connection part;

wherein the guide member includes a direction regulating portion on at least one of a side close to the opening of the branch member and a side close to the connection part such that (i) the distal end portion of the observation optical system to be disposed in the hard portion is guided from the opening to the connection part when the distal end portion of the observation optical system has a predetermined direction and (ii) the distal end portion of the observation optical system is prevented from being guided from the opening to the connection part when the distal end portion of the observation optical system has a direction different from the predetermined direction;

wherein the distal end portion of the observation optical system comprises an imaging module disposed in the hard portion, and the observation optical system further includes a cable unit extended from a proximal end of the imaging module; and wherein at least a part of the imaging module is formed asymmetrically with respect to the axis in the plane crossing the longitudinal direction of the observation optical system at right angles so that the direction of the imaging module with respect to the opening of the branch member is judged in a case where the imaging module is disposed in the hard portion through the opening of the branch member.

9. An endoscope main body for use in combination with an elongated observation optical system which is attachable to and detachable from the endoscope main body, wherein the elongated observation optical system includes a distal end portion formed asymmetrically with respect to an axis in a plane crossing a longitudinal direction of the observation optical system at right angles, the endoscope main body comprising:

an insertion section including:
an arm section having at least one bending portion;
a hard portion which is provided at a proximal end of the arm section, wherein the distal end portion of the observation optical system is disposable in the hard portion; and
another bending portion provided separately from the bending portion of the arm section;
wherein the insertion section is detachably attached to the observation optical system provided at a proximal end of the hard portion;

an operating section provided at a proximal end of the insertion section to operate the bending portion of the arm section;

another operating section provided at the proximal end of the insertion section to operate the other bending portion separately from the operating section which operates the bending portion of the arm section;

a wire disposed in the insertion section and connecting the bending portion of the arm section to the operating section;

another wire disposed in the insertion section and connecting the other bending portion to the other operating section, wherein the another wire is arrayed with the wire;

a branch member which includes a connection part connected to the proximal end of the insertion section, and which is provided at the proximal end of the insertion section such that (i) the operating section and the other operating section are branched from each other and (ii) the wire connected to the operating section and the other wire connected to the other operating section are branched from each other, the branch member having an opening as an inlet which guides the distal end portion of the observation optical system to the hard portion of the insertion section; and a guide member which is provided between the opening and the connection part of the branch member, and which guides the distal end portion of the observation optical system to be disposed in the hard portion from the opening of the branch member to the connection part;

wherein the guide member includes a direction regulating portion on at least one of a side close to the opening of the branch member and a side close to the connection part such that (i) the distal end portion of the observation optical system to be disposed in the hard portion is guided from the opening to the connection part when the distal end portion of the observation optical system has a predetermined direction and (ii) the distal end portion of the observation optical system is prevented from being guided from the opening to the connection part when the distal end portion of the observation optical system has a direction different from the predetermined direction;

wherein the endoscope main body further comprises a separation member which is provided in the branch member and which is configured to detachably attach the observation optical system to the insertion section while separating the wire and the other wire disposed in the insertion section from the observation optical system detachably disposed in the insertion section and while arraying the wires and the observation optical system; and wherein the guide member between the side close to the opening of the branch member and a side close to the separation member provided in the branch member is configured to prevent the observation optical system from rotating about the longitudinal direction of the observation optical system.

* * * * *